United States Patent [19]

Saito et al.

[11] Patent Number: 4,853,385
[45] Date of Patent: Aug. 1, 1989

[54] 7-N,8-N-ETHYLENEMITOMYCIN 8-IMINES

[75] Inventors: Yutaka Saito, Machida; Masaji Kasai, Fujisawa; Kunikatsu Shirahata, Komae; Motomichi Kono, Machida; Makoto Morimoto, Shizuoka; Tadashi Ashizawa, Numazu, all of Japan

[73] Assignee: Kyowa Hakko Kogyo Co., Ltd., Tokyo, Japan

[21] Appl. No.: 174,897

[22] Filed: Mar. 29, 1988

[30] Foreign Application Priority Data

Mar. 31, 1987 [JP] Japan ................. 62-78185

[51] Int. Cl.$^4$ ................ C07D 241/00; A61K 31/495
[52] U.S. Cl. ................... 514/250; 514/249; 548/422; 544/343; 544/342
[58] Field of Search ........ 514/250, 249; 548/422; 544/343, 342

[56] References Cited

U.S. PATENT DOCUMENTS

| | | | |
|---|---|---|---|
| 4,264,504 | 4/1981 | Urakawa et al. | 260/326.5 |
| 4,374,774 | 2/1983 | Kasai et al. | 548/422 |
| 4,395,558 | 7/1983 | Kasai et al. | 548/422 |
| 4,617,389 | 10/1986 | Remers | 544/142 |

FOREIGN PATENT DOCUMENTS

| | | |
|---|---|---|
| 122797 | 9/1979 | Japan . |
| 45322 | 3/1980 | Japan . |
| 118396 | 9/1980 | Japan . |
| 2134514 | 8/1984 | United Kingdom . |

OTHER PUBLICATIONS

Merck Index, 10th Ed. (1983), pp. 890–891, 1097.
J. Med. Chem., 26, 16–20 (1983).
J. Med. Chem., 26, 1453–57 (1983).

Primary Examiner—Nicholas S. Rizzo
Attorney, Agent, or Firm—Fitzpatrick, Cella, Harper & Scinto

[57] ABSTRACT

7-N,8-N-Ethylenemitomycin 8-imines represented by the formula

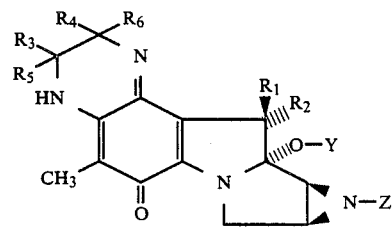

wherein one of the $R_1$ and $R_2$ represents carbamoyloxymethyl and another represents hydrogen or both are combined together to form methylene; $R_3$, $R_4$, $R_5$ and $R_6$ each independently represent hydrogen or $C_{1-4}$ alkyl, or $R_3$ and $R_4$ may be combined together to represent —$(CH_2)_n$—, wherein n is 3 or 4; and Y and Z represent hydrogen or methyl, provided that when $R_1$ represents carbamoyloxymethyl and Y represents methyl, $R_2$, $R_3$, $R_4$, $R_5$, $R_6$ and Z are not hydrogen simultaneously, has an excellent antitumor activity.

5 Claims, No Drawings

7-N,8-N-ETHYLENEMITOMYCIN 8-IMINES

BACKGROUND OF THE INVENTION

The present invention relates to 7-N,8-N-ethylenemitomycin 8-imines having an antitumor activity.

Mitomycins are generally known to be antibiotics having an antitumor activity. From the natural source, mitomycin C is mainly obtained, and as trace components, mitomycins A and B and porfiromycin (these are described in Merck Index, 10th edition) are obtained. Further, as trace components, mitomycins D and E as disclosed in Japanese Published Unexamined Patent Application No. 122797/79, mitomycins F and J as disclosed in Japanese Published Unexamined Patent Application No. 45322/80, mitomycins G, H and K as disclosed in Japanese Published Unexamined Patent Application No. 118396/80 and the like are also known. Structures of these mitomycins obtained from the natural source are shown in Table 1.

In addition, using the mitomycins described above as starting materials, mitomycins which are not available from the natural source are synthesized, and 9a-O-demethylmitomycin G as disclosed in Japanese Published Unexamined Patent Application No. 15408/80, 1a-demethylmitomycins G and K as disclosed in Japanese Published Unexamined Patent Application No. 7787/81, 9-epi-mitomycins B and D as disclosed in Japanese Published Unexamined Patent Application No. 30978/81 and the like are known. Structures of these mitomycins are shown in Table 2.

TABLE 2
Structures of Non-naturally Occurring Mitomycins

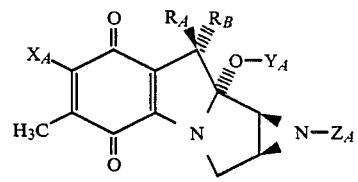

| Mitomycin | $X_A$ | $Y_A$ | $Z_A$ | $R_A$ | $R_B$ |
|---|---|---|---|---|---|
| 9a-O-Demethyl mitomycin G | $NH_2$ | H | $CH_3$ | Combined together to form $=CH_2$ | |
| 1a-Demethyl mitomycin G | $NH_2$ | $CH_3$ | H | Combined together to form $=CH_2$ | |
| 1a-Demethyl mitomycin K | $OCH_3$ | $CH_3$ | H | Combined together to form $=CH_2$ | |
| 9-Epi-mitomycin B | $OCH_3$ | H | $CH_3$ | $CH_2OCONH_2$ | H |
| 9-Epi-mitomycin D | $NH_2$ | H | $CH_3$ | $CH_2OCONH_2$ | H |

As compounds containing a 2-aminoethyl group at the 7-amino group, 7-N-(2-dimethylaminoethyl)mitomycin C as disclosed in Japanese Published Unexamined Patent Application No. 188590/82 and Journal of Medicinal Chemistry, 26, 16–20 (1983), 7-N-methyl-7-N-(2-methylaminoethyl)mitomycin C as disclosed in Japanese Published Unexamined Patent Application No. 152384/84, 7-N-methyl-7-N-(2-dimethylaminoethyl)mitomycin C as disclosed in Journal of Medicinal Chemistry, 26, 1453–1457 (1983), 7-N-(2-aminoethyl)-mitomycin C as disclosed in Journal of Medicinal Chemistry, 26, 16–20 (1983) (hereinafter referred to as Publication A) and Japanese Published Unexamined Patent Application No. 152384/84, etc. are mentioned. Among these mitomycins mentioned above, 7-N-(2-aminoethyl)mitomycin C is particularly relevant to the compound of the present invention. 7-N-(2-aminoethyl)mitomycin C is reported as Compound 13 in Publication A and as the compound illustrated in Example 22

TABLE 1
Structures of Mitomycins obtained from the Natural Source

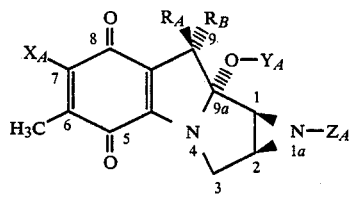

| Mitomycin | $X_A$ | $Y_A$ | $Z_A$ | $R_A$ | $R_B$ |
|---|---|---|---|---|---|
| A | $OCH_3$ | $CH_3$ | H | $CH_2OCONH_2$ | H |
| B | $OCH_3$ | H | $CH_3$ | H | $CH_2OCONH_2$ |
| C | $NH_2$ | $CH_3$ | H | $CH_2OCONH_2$ | H |
| D | $NH_2$ | H | $CH_3$ | H | $CH_2OCONH_2$ |
| E | $NH_2$ | $CH_3$ | $CH_3$ | H | $CH_2OCONH_2$ |
| F | $OCH_3$ | $CH_3$ | $CH_3$ | $CH_2OCONH_2$ | H |
| G | $NH_2$ | $CH_3$ | $CH_3$ | Combined together to form | $=CH_2$ |
| H | $OCH_3$ | H | $CH_3$ | Combined together to form | $=CH_2$ |
| J | $OCH_3$ | $CH_3$ | $CH_3$ | H | $CH_2OCONH_2$ |
| K | $OCH_3$ | $CH_3$ | $CH_3$ | Combined together to form | $=CH_2$ |
| Porfiromycin | $NH_2$ | $CH_3$ | $CH_3$ | $CH_2OCONH_2$ | H | of Japanese Published Unexamined Patent Application No. 152384/84.

According to Publication A, 7-N-(2-aminoethyl)-mitomycin C is reported as the compound having the following physicochemical properties: melting point (202 to 205° C., decomposed), elemental analysis (carbon: found, 47.41%; calculated as $C_{17}H_{23}N_5O_5 \cdot CH_2Cl_2$, 46.76%) and NMR [as signals derived from the 7-substituent ($H_2NCH_2CH_2NH-$) in $CDCl_3$, $\delta 1.47$ (brs, 2H), 3.50 (brs, 2H)]. From these data, however, it is difficult to positively support the structure of 7-N-(2-aminoethyl)mitomycin C. Based on physicochemical data given in Reference Example 1 of the present specification, especially MS, NMR spectrum, etc. which reflect the molecular formula, the structure of the compound as disclosed in Publication A should be corrected to be 7-N,8-N-ethylenemitomycin 8-imine (hereinafter referred to as Compound A).

As clear from the foregoing publications, Compound A and various mitomycins are known. However, even Compound A does not reach a satisfactory level of potency of antitumor activity and reduction in toxicity, and the development of better antitumor agents has been desired.

SUMMARY OF THE INVENTION

The 7-N,8-N-ethylenemitomycin 8-imines represented by the following formula (1) (hereinafter referred to as Compound I) have an excellent antitumor activity.

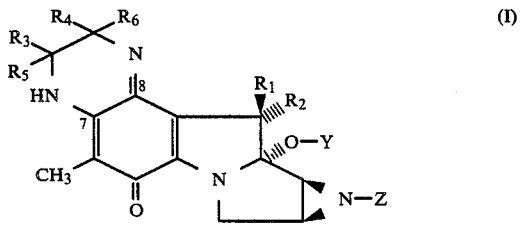

In the formula, one of $R_1$ and $R_2$ represents carbamoyloxymethyl and another represents hydrogen, or both are combined together to form methylene; $R_3$, $R_4$, $R_5$ and $R_6$ independently represent hydrogen or $C_{1-4}$ alkyl, or $R_3$ and $R_4$ may be combined together to form $-(CH_2)_n-$ wherein n is 3 or 4; and Y and Z independently represent hydrogen or methyl, provided that when $R_1$ represents carbamoyloxymethyl and Y represents methyl, $R_2$, $R_3$, $R_4$, $R_5$, $R_6$ and Z are not hydrogen simulataneously.

DESCRIPTION OF THE INVENTION

In the definitions of $R_3$, $R_4$, $R_5$ and $R_6$, the $C_{1-4}$ alkyl includes straight and branched chain alkyl group, for example, methyl, ethyl, i-propyl, n-butyl, etc.

A process for preparing Compound I is described below.

Compound I can be prepared by reacting mitomycin derivatives having an alkoxy group at the 7-position thereof with diamines (hereinafter referred to as Compound II)) represented by formula (II):

wherein $R_3$, $R_4$, $R_5$ and $R_6$ have the same significances as previously defined in an inert solvent. The reaction is considered to be a reaction of one amino group in Compound II with an alkoxy group at the 7-position of mitomycin and a condensation of the remaining amino group with the carbonyl group at the 8-position of mitomycin.

As the mitomycins having an alkoxy group, it is particularly preferred to utilize 7-methoxymitomycins.

Examples of 7-methoxymitomycins include mitomycins A, B, F, H, J and K, 1a-demethylmitomycin K, 9-epi-mitomycin B, etc. as illustrated in Tables 1 and 2.

As Compound II, mention may be made of ethylenediamine, 1,2-diaminopropane, 2,3-diaminobutane, 1,2-diamino-2-methylpropane, 2,3-diamino-2,3-dimethylbutane, 1,2-diaminocyclopentane, 1,2-diaminocyclohexane, etc.

As the solvent used for the reaction, ethereal solvents such as diethyl ether, tetrahydrofuran, etc.; aromatic hydrocarbons such as benzene, toluene, etc.; halogenated alkanes such as methylene chloride, chloroform, etc.; acetonitrile, ethanol, etc. are used alone or in combination. In particular, a solvent mixture of methylene chloride and ethanol is most preferred.

Compound II may be used generally in an equimolar amount to 7-methoxymitomycins but may also be used excessively in up to about 3 molar equivalents, for purposes of increasing the yield of Compound I.

The reaction is generally carried out at $-20°$ to $30°$ C. and completed in 2 to 48 hours, while it varies depending upon kind or amount of Compound II, etc.

In working up the reaction, the reaction solution is cooled as it is or after it is concentrated, and the formed solids are collected and recrystallized for purification. Alternatively, after concentration, the reaction solution can be purified by means of flash column chromatography, etc.

Acute toxicity and antitumor activity of typical examples of Compound I are shown below.

(A) Antitumor activity against sarcoma 180 solid tumor and acute toxitiy

Some compounds were chosen from Compound I, and antitumor activity ($ED_{50}$) against Sarcoma 180 solid tumor and acute toxicity ($LD_{50}$) were measured. The results are shown in Table 3.

Experiments were performed by the following methods.

(1) Effect on sarcoma 180 solid tumor

Sarcoma 180 cells of $5\times 10^6$ were intraperitoneally implanted into ddY mice. Seven days after, the cells were collected from the ascites. The cells were washed once with a sterile physiological saline, and the cells were suspended in sterile physiological saline to prepare a cell suspension containing $5\times 10^7$ cells per ml. 0.1 ml of the suspension was subcutaneously implanted into the right axilla of male ddY mice weighing $20\pm 2$ g. The test compound was dissolved in physiological saline with or without addition of Tween 80 and was administered intraperitoneally into each mouse of a group consisting of 5 mice at a dose of 0.1–0.2 ml, 24 hours after the implantation of the tumor cells.

The anti-tumor activity was determined in the following manner. 7 days after the implantation, the major axis (a) and the minor axis (b) of the tumor were measured to calculate a value of "$a\times b^2/2$" which corresponds to the volume of the tumor. The anti-tumor activity was expressed by the ratio (T/C) of the volume (T) of the tumors of the group of animals administered with the test compound to the corresponding volume (C) of tumors of the untreated animals.

(2) Determination of $ED_{50}$:

$ED_{50}$ shows the amount of the test compound needed for reducing the volume of Sarcoma 180 solid tumors in mice to 50% on the basis of the corresponding volume of Sarcoma solid tumors in control animals.

On graph paper, T/C was indicated by an arithmetic scale on the longitudinal axis and the administered amount of the test compound was indicated by a logarithmic scale on the lateral axis. The relationship between the dose and T/C was plotted by a straight line determined by the method of least squares, from which a dose corresponding to T/C of 0.5 was obtained.

(3) Acute toxicity:

Each animal of the test group consisting of 5 ddY mice was administered intraperitoneally once with a test compound. After the administration, the animals were observed for 14 days and deaths were noted. The $LD_{50}$ was determined by Beherns Kaerber's method.

TABLE 3

| Compound[1] | $LD_{50}$ (mg/kg) | $ED_{50}$ (mg/kg) | CI |
|---|---|---|---|
| 1 | 2.6 | 1.5 | 1.73 |
| 2 | 22.5 | 10.6 | 2.12 |
| 3 | 5.6 | 3.7 | 1.51 |
| 4 | 100 | 47.5 | 2.11 |
| A | 6.5 | 5.9 | 1.10 |

[1]Compounds 1 through 4 and A correspond to the compounds obtained in Examples 1 to 4 and Reference Example 1.

CI in the table indicates chemotherapy index and given by:

$$CI = LD_{50}/ED_{50}$$

As is clear from this definition, the CI value reflects selective toxicity against tumor. As the CI value is larger, the effect as an antitumor agent is more excellent, and from a clinical viewpoint, allowance of chemicals in dosage becomes broader. Therefore, the CI value is one of the most important indices in evaluation of antitumor agents.

Compound I has a larger CI value than Compound A and can be said to be excellent antitumor agents.

(B) Antitumor activity against lymphocytic leukemia P-338 and mitomycin C-resistant P-388

Some compounds were chosen from Compound I and antitumor activity against lymphocytic leukemia P-388 and mitomycin C-resistant P-388 was measured. The results are shown in Table 4.

The experiment was carried out by the following method.

From the peritoneal cavity of P-388 ascitic tumor-bearing mice (DBA/2) 7 days after the implantation, an ascitic fluid was collected. The cell number of P-388 in the ascitic fluid was counted, and the cells were suspended in sterile physiological saline to prepare a tumor cell suspension containing $5 \times 10^6$ cells/ml. 0.2 ml (containing $1 \times 10^6$ cells) of the suspension was implanted intraperitoneally into $CDF_1$ mice weighing 20 to 25 g. The test compound was intraperitoneally administered to each mouse of one test group consisting of 6 $CDF_1$ mice at a single dosage in 24 hours after the implantation of the tumor. 33-Day observation gave the survived life span for each mouse. Evaluation of the effect of the test compound was made by a ratio of a mean survival days after the implantation of the mice treated with the test compound to a mean survival days of the mice untreated with the test compound in the control group (Increased Life Span, ILS%). Then, ILS*, which is a ratio of ILS % of the test compound to ILS % of mitomycin C used as a reference compound under the same conditions, was calculated and shown in Table 4.

Further, the experiment was carried out in the same manner as above, using lymphocytic leukemia P-388 resistant to mitomycin C. The results are shown in Table 4. Evaluation of the effect of the test compound is shown by a ratio (ILS %) to a mean survival data of the control group (untreated mice).

TABLE 4

| | P-388 | | Mitomycin C-Resistant P-388 | |
|---|---|---|---|---|
| Compound | dose (mg/kg) | ILS* | dose(mg/kg) | ILS(%) |
| 1 | 1.5 | 0.60 | 1.5 | 135 |
| 5[2] | 1.25 | 0.56 | 1.25 | 144 |
| A | 100 | 0.43 | 100 | 107 |

[2]Compound 5 corresponds to the compound obtained in Example 5.

Compound I has ILS* and ILS value greater than those of Compound A and is an excellent compound.

Compound I may be used as the antitumor agent, if necessary, together with at least one pharmaceutical diluent, auxiliary agent or carrier. For example, each compound is dissolved in physiological saline, glucose injection solution, lactose injection solution or mannitol injection solution and is intravenously administered to mammals, especially to human beings, in a dose of 0.06 to 5 mg/kg. Further, in the same dose, Compound I may also be administered intraarterially, intraperitoneally or intrapleurally. Compound I may also be freeze-dried according to the Japanese Pharmacopoeia, or the compound may be mixed with sodium chloride to prepare a powder preparation for injection. In addition, the antitumor agent may also contain well known pharmaceutically acceptable diluents such as Linger's solution, auxiliary agents such as polyethylene glycol, HCO-60 (surfactant, manufactured by Nikko Chemical Co., Ltd.), ethanol and/or carrier such as liposome and cyclodextrin. Dosage may appropriately vary depending upon age and condition. Administration schedule may also be varied depending upon condition and dose, and for example, intermittent administration once a week or once every three weeks is possible. In the same dosage and the same administration route, oral administration and rectal administration are also possible. Upon oral administration, the compound may be administered as tablets, powders, granules, syrups, suppositories, etc., together with appropriate auxiliary agents.

Hereinafter, examples and reference examples are given.

Physicochemical data of each compound were measured by the following instruments.

MS: Hitachi M-80B (measured by the SI method)

IR: Shimadzu IR-27-G, Nippon Bunko IR-810 (measured by the KBr method)

$^1$H-NMR: JEOL PS-100 (100 MHz), JEOL FX-100 (100 MHz), Bruker AM-400 (400 MHz) (measured in pyridine-$d_5$ or chloroform-d)

Structures of representative Compound I and Compound A synthesized are shown in Table 5.

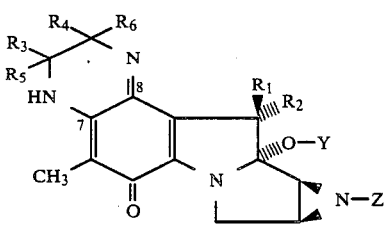

(I)

d, J=12.5), 4.98 (1H, dd, J=10.5, 11.5), 5.55 (1H, dd, J=10.5, 4.4) 7.32 (1H, bs), 7.60 (2H, bs).

EXAMPLES 2 through 5

Compounds identified in Table 6 were obtained in a manner similar to Example 1 except that the starting materials (mitomycin F and ethylenediamine) used in Example 1 were replaced by starting materials shown in Table 6. Physicochemical properties of these compounds are shown in Table 7.

TABLE 5

| Compound | $R_1$ | $R_2$ | $R_3$ | $R_4$ | $R_5$ | $R_6$ | Y | Z |
|---|---|---|---|---|---|---|---|---|
| 1 | $CH_2OCONH_2$ | H | H | H | H | H | $CH_3$ | $CH_3$ |
| 2 | H | $CH_2OCONH_2$ | H | H | H | H | H | $CH_3$ |
| 3 | H | $CH_2OCONH_2$ | H | H | H | H | $CH_3$ | $CH_3$ |
| 4 | combined together to form =$CH_2$ | | H | H | H | H | H | $CH_3$ |
| 5 | $CH_2OCONH_2$ | H | $(CH_2)_4$ | | H | H | $CH_3$ | $CH_3$ |
| A | $CH_2OCONH_2$ | H | H | H | H | H | $CH_3$ | H |

EXAMPLE 1

At first, 100 mg of mitomycin F was dissolved in 5 ml of methylene chloride-ethanol (4:1, v/v), and 30 μl of ethylenediamine was added to the solution. The mixture was stirred at 25° C. for 4.5 hours and allowed to stand at −15° C. for 17 hours. The solid formed was filtered. After washing with a small quantity of methylene chloride-ethanol (4:1, v/v), the solid was dried at 35° C. in vacuum for 17 hours to give 83.2 mg (yield, 81.0%) of 7-N,8-N-ethyleneporfiromycin 8-imine (Compound 1).

Appearance: dark purple powder,

MS: m/z 375=$M^+$+2, $C_{18}H_{23}N_5O_4$=373.

IR ($cm^{-1}$): 3450, 3320, 3270, 2940, 2860, 1710, 1610, 1560, 1545, 1415, 1325, 1315, 1210, 1060, 1030.

$^1$H-NMR (δppm): (100 MHz, Py-$d_5$), 1.96 (3H, s), 2.13 (1H, dd, J=4.6, 2.2), 2.29 (3H, s), 2.59 (1H, d, J=4.6), 3.09 (2H, m), 3.28 (3H, s), 3.56 (1H, dd, J=12.5, 2.2), 3.79 (2H, m), 4.06 (1H, dd, J=11.5, 4.4), 4.39 (1H,

TABLE 6

| Example | Starting Materials | Product | Yield mg (%) |
|---|---|---|---|
| 2 | Mitomycin B (102 mg) Ethylenediamine (31 μl) | 7-N,8-N—Ethylene-mitomycin D 8-imine (Compound 2) | 56.5 (53.9) |
| 3 | Mitomycin J (154 mg) Ethylenediamine (28 μl) | 7-N,8-N—Ethylene-mitomycin E 8-imine (Compound 3) | 81.0 (51.2) |
| 4 | Mitomycin H (100 mg) Ethylenediamine (38 μl) | 9a-O—Demethyl-7-N,8-N—ethylene-mitomycin G 8-imine (Compound 4) | 73.8 (71.4) |
| 5 | Mitomycin F (200 mg) 1,2-Diamino-cyclohexane[3] (200 μl) | 7-N,8-N—(1,2-Cyclo-hexylene) porfiromycin 8-imine (Compound 5) | 87.8 (37.3) |

[3]Mixture of 60% cis-form and 38% of DL-trans-form

TABLE 7

| Compound | Appearance | MS | IR ($cm^{-1}$) | $^1$H—NMR (δppm) |
|---|---|---|---|---|
| 2 | dark red purple powders | m/z 362 = $M^+$+3 $C_{17}H_{21}N_5O_4$ = 359 | 3420,2950, 1715,1700, 1640,1605, 1565,1450, 1400,1330, 1220,1085 | (400MHz,Py-$d_5$) 1.93(3H,s), 2.11(3H,s), 2.16(1H,dd, J=4.7, 2.0), 2.50 (1H, d, J=4.7) 3.01(2H,m), 3.64(1H, ddd,J=17.7,9.6,6.2),3.66(1H, dd,J=12.5,2.0), 3.88(1H, dt, 17.7,4.7), 4.39(1H,dd,J=8.9, 3.0) 4.43(1H,d,J=12.5), 5.34(1H,dd,J=10.1,8.9), 5.53 (1H,dd,J=10.1,3.0), 7.21(1H, bs), 7.42(2H,bs), 7.6(1H,bs) |
| 3 | dark red purple powders | m/z 375 = $M^+$+2 $C_{18}H_{23}N_5O_4$ = 373 | 3415,2945, 2885,1715, 1705,1610, 1580,1560, 1535,1400, 1310,1065, 1035 | (400MHz,Py-$d_5$) 1.94(3H,s), 2.09(3H,s),2.18(1H,dd, J=4.4, 2.2), 2.25(1H,d, J=4.4), 3.06(2H,m), 3.41(3H, s), 3.63(1H,ddd, J=17.7, 9.8, 7.4), 3.67(1H, dd,J=12.3, 2.2), 3.92(1H,dt, J=17.7, 4.7), 4.14 (1H,d, J=12.3), 4.40(1H,dd, J=10.1, 3.2), 5.04(1H, t, J=10.1), 5.58(1H. dd, J=10.1,3.2), 7.28(1H, bs), 7.40(2H, bs) |
| 4 | dark green powders | m/z 300 = $M^+$+2 $C_{16}H_{18}N_4O_2$ = 298 | 3285,2940 1630,1600, 1545,1320, 1210,1080, 1040 | (400MHz,Py-$d_5$) 1.92(3H,s), 2.14(3H,s), 2.23(1H,dd, J=4.7,2.0), 2.63 (1H,d, J=4.7), 3.04 (2H,m), 3.74 (1H,dd,J=12.8,2.0), 3.82(2H t,J=6.5), 4.67(1H,d,J=12.8), |

TABLE 7-continued

| Compound | Appearance | MS | IR (cm$^{-1}$) | $^1$H—NMR ($\delta$ppm) |
|---|---|---|---|---|
| 5 | grayish purple powders | m/z 429 = M$^+$+2 C$_{22}$H$_{29}$N$_5$O$_4$ = 427 | 3430,3350, 2940,2855, 1710,1610, 1565,1555, 1540,1445, 1335,1310, 1060 | 5.94(1H,d,J=2.0), 6.75(1H, d,J=2.0), 7.36(1H,s), 8.31 (1H,bs) (100MHz,CDCl$_3$) Mixture of 4 diastereoisomers (ca.37:37:15:11) major sharp peaks: 1.72(3H,s), 2.24, 2.26 (total ca. 3H, each s), 3.17, 3.20, 3.21, 3.23 (total 3H, each s) |

EXAMPLE 6

At first, 1 g of Compound 1 was dissolved in 1000 ml of distilled water, and the solution was filtered under pressure through a millipore filter (pore diameter of 0.22μ) to sterilize it. Into brown vials, 1.0 ml each of the resulting sterile filtrate was pipetted (1 mg of main component/vial). After freeze-drying at −50° C. for 2 hours, primary drying was performed at −10° 1 C. of shelf temperature in a vacuum of 0.1 mmHg for 24 hours. After it was ascertained that the shelf temperature was identical with an article temperature, secondary drying was performed at 30° C. of shelf temperature in a vacuum of 0.1 mmHg for 4 hours to remove moisture. Each vial was stoppered with a rubber stopper. Upon use, 5 ml of sterile physiological saline was added and the compound was dissolved with shaking and stirring to prepare an injection.

REFERENCE EXAMPLE 1

At first, 47 mg of mitomycin A and 15 μl of ethylenediamine were dissolved in 4 ml of methylene chlorideethanol (4:1, v/v). The solution was stirred at 25° C. for 2.5 hours and subsequently treated in a manner similar to Example 1. Thus, 40 mg (yield, 81.5%) of 7-N,8-N-ethylenemitomycin C 8-imine was obtained.

Appearance: dark purple powders.

MS: m/z 361=M$^+$+2, C$_{17}$H$_{21}$N$_5$O$_4$=359.

IR (cm$^{-1}$): 3420, 3300, 2940, 1720, 1690, 1620, 1605, 1565, 1545, 1410, 1320, 1055.

$^1$H-NMR ($\delta$ppm): (100 MHz, Py-d$_5$), 1.96 (1H, bs), 1.96 (3H, s), 2.73 (1H, bd, J=3.2), 3.12 (2H+1H, m), 3.31 (3H, s), 3.64 (1H, dd, J=12.4, 2.2), 3.76 (2H, m), 4.11 (1H, dd, J=11.0, 4.4), 4.47 (1H, d, J=12.4), 5.21 (1H, t, J=11.0), 5.65 (1H, dd, J=11.0, 4.4), 7.31 (1H, bs), ca.7.6 (2H, bs) (400 MHz, CDCl$_3$) 0.51 (1H, bs), 1.72 (3H, s), 2.78 (1H, bs), 2.92 (1H, bs), 3.24 (3H, s), 3.29 (2H, m), 3.47 (1H, bd, J=ca.12), 3.67 (1H, dd, J=11.0, 3.8), 3.82 (1H, ddd, J=17.7, 9.6, 6.4), 4.00 (1H, dt, J=17.7, 5.2), 4.08 (1H, bd, J=ca.12), 4.59 (2H, bs), 4.74 (2H, bs), 4.97 (1H, bd, J=7.4).

REFERENCE EXAMPLE 2

Preparation of Compound A according to the method described in the publication is as follows.

Using 50 mg of mitomycin A, 26.2 mg (yield, 50.9%) of Compound A was obtained by the same procedure as in Compound 13 of Publication A.

What is claimed is:

1. 7-N,8-N-ethylenemitomycin 8-imines represented by formula (I):

wherein one of $R_1$ and $R_2$ represents carbamoyloxymethyl and the other represents hydrogen, or both are combined together to form methylene; $R_3$, $R_4$, $R_5$ and $R_6$ independently represent hydrogen or C$_{1-4}$ alkyl, or $R_3$ and $R_4$ are combined together to represent —(CH$_2$)$_n$—, wherein n is 3 or 4; and Y and Z represent hydrogen or methyl, provided that when $R_1$ represents carbamoyloxymethyl and Y represents methyl, $R_2$, $R_3$, $R_4$, $R_5$, $R_6$ and Z are not hydrogen simultaneously.

2. A compound according to claim 1, wherein $R_3$, $R_4$, $R_5$ and $R_6$ are hydrogen and Z is methyl.

3. A compound according to claim 1, wherein $R_3$ and $R_4$ are combined together to represent —(CH$_2$)$_4$—, and $R_5$ and $R_6$ are hydrogen.

4. A compound selected from the group consisting of 7-N,8-N-ethyleneporfiromycin 8-imine, 7-N,8-N-ethylenemitomycin D 8-imine, 7-N,8-N-ethylenemitomycin E 8-imine, 9a-O-demethyl-7-N,8-N-ethylenemitomycin G 8-imine and 7-N,8-N-(1,2-cyclohexylene)porfiromycin 8-imine.

5. An anti-tumor agent which comprises a pharmaceutically acceptable carrier and an effective anti-tumor amount of the compound defined in claim 1.

* * * * *